(12) United States Patent
Msika et al.

(10) Patent No.: US 8,747,815 B2
(45) Date of Patent: Jun. 10, 2014

(54) USE OF A COSMETIC OF PHARMACEUTICAL COMPOSITION, COMPRISING A LUPEOL-RICH EXTRACT AS AN ACTIVE INGREDIENT FOR STIMULATING THE SYNTHESIS OF HEAT SHOCK PROTEINS

(75) Inventors: Philippe Msika, Versailles (FR); Antoine Piccirilli, Versailles (FR); Nathalie Piccardi, Arceau (FR)

(73) Assignee: Laboratoires Expanscience, Courbevoie (FR)

( * ) Notice: Subject to any disclaimer, the term of this patent is extended or adjusted under 35 U.S.C. 154(b) by 1553 days.

(21) Appl. No.: 10/564,785

(22) PCT Filed: Jul. 19, 2004

(86) PCT No.: PCT/FR2004/001907
§ 371 (c)(1),
(2), (4) Date: Jan. 17, 2006

(87) PCT Pub. No.: WO2005/009331
PCT Pub. Date: Feb. 3, 2005

(65) Prior Publication Data
US 2006/0216249 A1 Sep. 28, 2006

(30) Foreign Application Priority Data

Jul. 18, 2003 (FR) .................................. 03/08796

(51) Int. Cl.
*A61K 8/97* (2006.01)
*A61K 36/48* (2006.01)
*A61K 31/045* (2006.01)
*A61Q 19/00* (2006.01)
*A61Q 11/00* (2006.01)

(52) U.S. Cl.
CPC . *A61K 8/97* (2013.01); *A61K 36/48* (2013.01); *A61K 31/045* (2013.01); *A61Q 19/00* (2013.01); *A61Q 11/00* (2013.01)
USPC ............................................ 424/58; 424/757

(58) Field of Classification Search
None
See application file for complete search history.

(56) References Cited

U.S. PATENT DOCUMENTS

| | | | | |
|---|---|---|---|---|
| 5,190,979 | A * | 3/1993 | Herman | 514/762 |
| 5,972,999 | A * | 10/1999 | Murad | 514/474 |
| 6,146,616 | A * | 11/2000 | Msika et al. | 424/59 |
| 2004/0121030 | A1 * | 6/2004 | Piccirilli et al. | 424/757 |

FOREIGN PATENT DOCUMENTS

| | | |
|---|---|---|
| FR | 2 778 565 A | 11/1999 |
| WO | WO 98/47479 A | 10/1998 |

OTHER PUBLICATIONS

Gogly et al. "Effects of vegetable extract from lupinus albus (Lu105) on the degradation by human leucocyte elastase and bacterial collagenase of gingival collagen and elastic fibers", Journal of Investigative dermatology, vol. 119, No. 1, Jul. 2002, p. 232, XP002286368.*
Hernandez-Perez et al., Dermatol. Surg., 2002, 28(12), pp. 1124-1130.*
Malini et al., "Protective effect of triterpenes on calcium oxalate crystal-induced peroxidative changes in experimental urolithiasis," Pharmacological Research, Apr. 2000, vol. 41, No. 4, pp. 413-418 (Abstract).
Saleem et al., "Lupeol, a triterpene, inhibits early responses of tumor promotion induced by benzoyl peroxide in murine skin," Pharmacological Research, 2001, vol. 43, No. 2, pp. 127-134.
De Medrano Villar et al., "Triterpenoid compounds from Araujia sericifera B. Effects on the isolated guinea pig ileum," Methods Find. Exp. Clin. Pharmacol., 1997, vol. 19, No. 8, pp. 515-520 (Abstract).
De Miranda et al., "Anti-inflammatory and analgesic activities of the latex containing triterpenes from Himatanthus sucuuba," Planta Med, Apr. 2000, vol. 66, No. 3, pp. 284-286 (Abstract).
Kahlos et al., "Preliminary tests of antiviral activity of two Inonotus obliquus strains," Fitoterapia, 1996, vol. 67, No. 4, pp. 344-347 (Abstract).
Nagaraj et al., "Effect of lupeol, a pentacyclic triterpene, on the lipid peroxidation and antioxidant status in rat kidney after chronic cadmium exposure," J. Appl. Toxicol., Sep. 2000, vol. 20, No. 4, pp. 413-417 (Abstract).
Singh et al., "Anti-inflammatory activity of lupeol," Fitoterapia, 1997, vol. 68, No. 1, pp. 9-16 (Abstract).
Zachariah et al., "Anti-inflammatory and anti-mitotic activities of lupeol isolated from the leaves of Ixora coccinea Linn.," Ind. J. Pharm. Sci. 1994, vol. 56, No. 4, pp. 129-132 (Abstract).

* cited by examiner

*Primary Examiner* — Brian Gulledge
(74) *Attorney, Agent, or Firm* — Foley & Lardner LLP (57) ABSTRACT

The present invention relates to the use of a lupeol-rich extract for the production of a cosmetic or pharmaceutical composition for treating and/or preventing a connective tissue degeneration. Said invention also relates to the use of a lupeol-rich extract for the production of a pharmaceutical composition for preventing and/or treating non-inflammatory articular pathologies, periodontal diseases and stretch marks. The invention also relates to the use of a lupeol-rich extract for the production of a cosmetic composition as a cicatrizing agent, a restructuring agent and an anti-sagging agent for skin and/or mucosae.

10 Claims, 3 Drawing Sheets

USE OF A COSMETIC OF PHARMACEUTICAL COMPOSITION, COMPRISING A LUPEOL-RICH EXTRACT AS AN ACTIVE INGREDIENT FOR STIMULATING THE SYNTHESIS OF HEAT SHOCK PROTEINS

The present invention relates to the use of a lupeol-rich extract for the production of a pharmaceutical or cosmetic composition for treating and/or preventing a connective tissue degeneration.

Lupin is quite a widespread plant that is found in Europe, in Asia and in North and South America. This plant is closely related to the pea, the broad bean, the soybean and the bean. Several lupin species can be mentioned as being the most well known: *lupinus albus* (white lupin), *lupinus angustifolius* (blue lupin), *lupinus luteus* (yellow lupin), *lupinus mutabilis* (pearl lupin), *lupinus graecus, lupinus micranthus Guss, lupinus hispanicus, lupinus pilosus, lupinus cosentinii, lupinus atlanticus, lupinus princei* and *lupinus somaliensis*. One of the most common species in Europe is the sweet white lupin (*lupinus albus*), in particular the variety Arès exhibiting the pauper gene.

Lupeol (1) belongs to the triterpene family, and more particularly to the triterpenic alcohol family.

(1)

Lupeol is of definite interest by virtue of its many biological activities. It is in particular known for its anti-inflammatory (Singh S. et al., *Filoterapia*, 1997, 68, No. 1, 9) and analgesic (De Miranda A. L. et al., *Planta Med*, 2000, 66(3), 284) properties, its nephroprotective action with respect to heavy metals (Nagaraj M. et al., *J. Appl. Toxicol*, 2000, 20(5), 413), its antihistamine action (De Medrano Villar M. J. et al., *Methods Find Exp. Clin. Pharmacol.*, 1997, 19, No. 8, 515), and its antimitotic (Zachariah R. et al., *Indian J. Pharm. Sci.*, 1994, 56, No. 4, 129) and antiviral (Kahlos K., *Filoterapia*, 1996, 67, No. 4, 344) activities.

Lupeol is also known for its antioxidizing properties. Specifically, lupeol activates the regeneration of antioxidizing enzymes in the skin that have been damaged by environmental toxins. Furthermore, it is a chemopreventive agent of the skin and it makes it possible to suppress toxicity induced by benzoyl peroxide in the skin (Saleem M, et al., 2001, Lupeol, a triterpene, inhibits early responses of tumor prevention induced by benzoyl peroxide in murine skin, *Pharmacol Res*, 43(2):127-134).

Lupeol makes it possible to control keratinocyte proliferation, and it can therefore be used in anti-inflammatory compositions.

It has also been found that lupeol makes it possible to effectively reduce the risks of kidney stone formation, and it is therefore used in the treatment of urinary diseases (Malini M M, et al. (2000) Protective effect of triterpenes on calcium oxalate crystal induced peroxidative changes in experimental urolithiasis. *Pharmacol Res*. 41(4):413-418).

Lupeol can also be used as a synthesis intermediate, in particular for the preparation of phytohormones and of steroid analogs.

Lupeol is present in many plants, such as *Aloe vera* or the bark of *Crataeva nurvala*. It has been isolated on several occasions from various plants such as "Bresk".

It has also been extracted from lupin pods. Patent application FR 2 822 821 describes an extract of lupin seed pods containing lupeol; advantageously, the extract has a lupeol content of greater than 30% by weight, preferably greater than 50% by weight. Even more advantageously, the extract of lupin seed pods has a lupeol content of between 70 and 100%.

Patent application FR 2 822 821 also describes a method for obtaining an extract of lupin seed pods, which comprises at least the series of steps below:
grinding the lupin pods,
extracting the total lipids contained in the ground lupin pods using an organic solvent chosen from the group consisting of aliphatic alkanes, aromatic alkanes, aliphatic alcohols, and halogenated derivatives thereof, and
purifying the lipids obtained so as to obtain a lupeol-rich extract.

Heat shock proteins (HSP, heat stress or shock protein, family), hereinafter referred to as heat shock proteins and abbreviated to HSPs, are present in all organisms from bacteria to humans. Five major HSP groups exist, characterized by their molecular weight:
20-30 kDa;
50-60 kDa;
70 kDa;
90 kDa; and
100-110 kDa.

Ubiquitin and heme oxygenase also belong to the major HSP family.

HSPs are expressed constitutionally under physiological conditions and have basic activities essential for protein synthesis, while at the same time protecting the cells from numerous attacks such as a temperature increase, ultraviolet radiation, ischemia-reperfusion and apoptosis.

The chaperone function of HSPs is one of the major protein functions to have been discovered. Initially demonstrated in the context of a heat shock, the presence of these proteins at an already considerable level in all cells in the absence of shock suggested that they contributed to the normal folding of proteins. These chaperones are capable of inhibiting the aggregation of partially denatured proteins and of folding them using ATP. They prevent inappropriate protein associations, and are involved in the intracellular transport and the secretion of proteins.

HSP47 is a protein located in the endoplasmic reticulum of cells (protein synthesis compartment) and it binds specifically to various types of collagen and procollagen, in particular type I, II, III, IV and V. HSP47 is involved in the "quality control system" of the cell, preventing the latter from secreting procollagen with an inadequate structure. A correlation between overexpression of collagen and of HSP47 has been demonstrated in humans.

Collagens represent approximately 30% of total proteins and are the major constituents of the extracellular matrix of connective tissues such as the dermis (70% of extracellular matrix proteins), cartilage or the gingival connective tissue (60 to 65% of proteins). To date, 19 different types of collagen have been described. By definition, they have triple helix domains in varying proportions and form organized structures within the extracellular matrix, such as fibrils, filaments or networks. Collagens are synthesized from a procollagen by connective cells such as dermal and gingival fibroblasts, and also by chondrocytes in articular cartilage. The collagen fibers synthesized become strengthened and assemble into bundles that constitute the definitive and insoluble collagen fiber, which will be able to respond in the future to tensile stresses.

Connective tissues play a major role as a carrier and support for the other elements constituting the organ and as a shock absorber. For example, the gingival connective tissue provides support for the teeth. In the skin, the dermis is in particular responsible for the firmness of the skin.

A connective tissue degeneration, related to an impairment of the collagen network, such as an inhibition of collagen and/or procollagen synthesis, an incorrect synthesis of collagen and/or procollagen, collagen fiber degradation, or a decrease in the number of fibroblasts and in their metabolism, can therefore have important consequences.

The applicant has discovered that a lupeol-rich extract can also be used for stimulating the synthesis of heat shock proteins, and more particularly for simulating the synthesis of HSP47 (Heat Shock Protein 47), in order to treat and/or prevent connective tissue degeneration relating to internal processes and/or to outside attacks.

The applicant has thus discovered that a lupeol-rich extract can make it possible to control the normal structure of collagen, via the stimulation of HSP47 synthesis, when the skin and/or the joints and/or the gingival connective tissues are subjected to a shock-inducing environment. This shock-inducing environment may be a physical constraint, induced, for example, by a weight gain that may in particular lead to a variation in the phenotype and in the metabolism of fibroblasts, exposure to radiation, in particular to UV-radiation, senescence or inflammation.

For the purpose of the present invention, the term "lupeol-rich extract" is intended to mean an extract having a lupeol content of greater than 30% by weight, advantageously greater than 50% by weight, and even more advantageously between 70 and 100% by weight.

The main subject of the present invention is the use of a lupeol-rich extract for the production of a cosmetic or pharmaceutical composition for treating and/or preventing connective tissue degeneration in the dermis and/or the cartilage and/or the gingival connective tissue, related to a collagen production anomaly.

A lupeol-rich extract according to the present invention can thus be used in a cosmetic composition for treating and/or preventing connective tissue degeneration in the dermis and/or the cartilage and/or the gingival connective tissue.

A lupeol-rich extract can also be used for the production of a medicinal product for treating and/or preventing connective tissue degeneration in the dermis and/or the cartilage and/or the gingival connective tissue.

In the context of the present invention, reference will be made without distinction to a pharmaceutical composition or a drug.

For the purpose of the present invention, the expression "collagen production anomaly" is intended to mean an insufficient synthesis of collagen and/or of procollagen by fibroblasts or chondrocytes, an incorrect synthesis of collagens and/or of procollagens, collagen fiber degradation, or a decrease in the number of fibroblasts or of chondrocytes and in their metabolism.

For the purpose of the present invention, the term "incorrect synthesis" of collagen is intended to mean any synthesis of a collagen or procollagen exhibiting structural anomalies, that can no longer in particular perform its function of mechanical support for the skin and/or the joints and/or the gingival connective tissues.

The collagen production anomaly may be induced by an internal or external shock factor. For example, under a physical constraint, such as a weight gain, excess weight, or a distention of the tissues in particular in the context of a pregnancy, subsequent to an irradiation, in particular with ultraviolet rays, subsequent to an inflammation or in a state of senescence, the fibroblasts or the chondrocytes, subjected to these external constraints, may synthesize collagen with an abnormal structure.

The collagen production anomaly may in particular be an inhibition of the synthesis or an incorrect synthesis of procollagens and collagens, in particular of procollagens and/or collagens type I, II, III, IV or V.

The lupeol-rich extract according to the present invention plays the role of a promoter of heat shock protein synthesis, in particular of HSP47 synthesis. This activation of heat shock proteins, advantageously of HSP47, makes it possible to stimulate the metabolism and the proliferation of fibroblasts and of chondrocytes and thus to combat and/or prevent degeneration of the collagen network.

The cosmetic composition according to the invention is for stimulating the synthesis of heat shock proteins, HPSs, in particular the synthesis of HSP47, and thus the activity of fibroblasts and of chondrocytes.

The pharmaceutical composition or the drug according to the invention is for stimulating the synthesis of heat shock proteins, HSPs, in particular the synthesis of HSP47, and thus the activity of fibroblasts and of chondrocytes.

According to an advantageous embodiment of the invention, the pharmaceutical composition or the drug is for treating and/or preventing articular pathologies, in particular non-inflammatory articular pathologies.

Articular pathologies are characterized by an imbalance between the synthesis and the degradation of the extracellular matrix that surrounds the chondrocytes. The articular cartilage, which consists mainly of a network of collagen fibers, of a gel of hydrophilic proteoglycans and of chondrocytes, plays a double mechanical role that is essential for the protection of the subchondral bone. Firstly, it decreases the rubbing forces when the bone segments move and, secondly, it ensures the transmission, distribution and absorption of the stresses to which the joint is subjected. Once adulthood has been reached, the amount of renewal of the collagen network within the articular cartilage is very small. It is therefore important to be able to stimulate the synthesis of collagens and of procollagens and/or to attenuate an impairment of the collagen network, which are the major constituents of cartilage. The pharmaceutical composition according to the present invention makes it possible to stimulate the synthesis of HSP47, which thus makes it possible to combat and/or prevent degeneration of the connective tissue of the articular cartilage.

Advantageously, the drug according to the invention is for preventing and/or treating arthrosis, which may be due to a primary lesion of the cartilage with modification of the structure of the connective tissues and a decrease in proteoglycans.

The drug or the pharmaceutical composition according to the invention is also for preventing and/or treating periodontal diseases. In particular, the pharmaceutical composition according to the invention is for preventing and/or treating gingivitis or periodontitis.

Periodontal diseases, the ultimate consequence of which is loss of the tooth, are in particular reflected by a degeneration of gingival connective tissues. The gingival connective tissue is composed of 60 to 65% of collagens. The pharmaceutical composition according to the present invention makes it possible to combat and/or prevent degeneration of the gingival connective tissue, via a stimulation of HSP47 synthesis, which will make it possible to promote collagen expression.

According to another advantageous embodiment of the invention, the drug according to the invention is for preventing and/or treating stretch marks.

Stretch marks can be considered as an effect on the fibroblast cell, characterized in particular by an inhibition of the expression of the genes encoding fibronectin, collagen type I and collagen type II, and the conversion of fibroblasts to myofibroblasts under the effect of the mechanical distensions. This collagen tissue degeneration results in the formation of an atrophic dermal scar. One of the main initiating factors is mechanical stress.

The pharmaceutical composition according to the present invention is advantageously for topical application. The term "topical application" is intended to mean application of the composition both to the skin and to the buccal region, in particular to the gums.

The pharmaceutical composition according to the invention is characterized in that the concentration of lupeol-rich extract is between 0.001% and 10% by weight, advantageously between 0.1 and 10% by weight, in particular between 1 and 5% by weight, relative to the total weight of the pharmaceutical composition.

The cosmetic composition according to the present invention makes it possible to promote the resistance to shock(s) and to mechanical stresses of the skin and/or of the joints and/or of the gingival connective tissues.

Said cosmetic composition allows the connective tissues to withstand stress under a physical constraint, such as a weight gain, excess weight, or a distension of the tissues in particular in the context of a pregnancy, or irradiation, in particular ultraviolet irradiation.

According to an advantageous embodiment of the invention, the cosmetic composition is useful as a cicatrizing agent for the skin and/or the joints and/or the gingival connective tissues and/or the mucous membranes. This is because the cosmetic composition according to the invention makes it possible to stimulate the activity of fibroblasts and of chondrocytes, which synthesize the collagen necessary to make up for the loss of substance with a new tissue.

The cosmetic composition is advantageously used in particular for preventing and/or treating stretch marks or their appearance.

According to another advantageous embodiment of the invention, the cosmetic composition is useful as a restructuring agent for the skin and/or the mucous membranes.

The cosmetic composition is also advantageously useful as an anti-sagging agent for the skin and/or the mucous membranes. Skin aging is in particular characterized by a decrease in the number of fibroblasts and by a decrease in their activity. The cosmetic composition according to the invention makes it possible to stimulate the metabolism and the proliferation of fibroblasts. It is therefore advantageously used for preventing and/or delaying chronological skin aging, extrinsic skin aging, in particular due to the sun, to tobacco, to pollution or to stress, and menopausal skin aging.

The cosmetic composition according to the invention acts on the dermis of the skin.

According to an advantageous variant of the invention, the cosmetic composition is intended for pregnant women.

The cosmetic composition may also be used as a mouthwash or toothpaste.

For the purpose of the present invention, the expression "toothpaste" includes all conventional dentifrice formulations, whether in particular in the form of a tooth gel, of a toothpaste or of a toothpaste and gel combination.

The cosmetic composition is advantageously for topical application. The term "topical application" is intended to mean application of the composition both to the skin and to the buccal region, in particular to the gums.

The cosmetic composition according to the invention is characterized in that the concentration of lupeol-rich extract is between 0.001% and 10% by weight, advantageously between 0.1 and 10% by weight, in particular between 1 and 5% by weight, relative to the total weight of the cosmetic composition.

The lupeol-rich extract has a lupeol content of greater than 30% by weight, advantageously greater than 50% by weight, and even more advantageously between 70 and 100% by weight.

Thus, the cosmetic composition according to the invention is characterized in that the lupeol concentration is between 0.0003 and 10% by weight, advantageously between 0.007 and 10% by weight, relative to the total weight of the cosmetic composition.

The composition which makes it possible to implement the invention comprises a cosmetically acceptable carrier, i.e. a carrier which is compatible with the skin, and may be in any of the pharmaceutical forms normally used for topical application, in particular in the form of an aqueous, aqueous-alcoholic or oily solution, of an oil-in-water or water-in-oil or multiple emulsion, of an aqueous or oily gel, or a liquid, pasty or solid anhydrous product, of a dispersion of oil in an aqueous phase by means of spherules, it being possible for these spherules to be polymeric nanoparticles such as nanospheres and nanocapsules, or better still lipid vesicles of ionic and/or nonionic type, or of a transdermal device, or in any other form for topical application.

This composition may be more or less fluid and may have the appearance of a white or colored cream, of an ointment, of a milk, of a lotion, of a serum, of a paste, of a foam or of a gel.

It may optionally be applied to the skin in the form of an aerosol. It may also be in solid form, and for example in the form of a stick. It may also be applied by means of a patch.

Advantageously, the cosmetically acceptable medium is an oily solution, a water-in-oil emulsion, an oil-in-water emulsion, a microemulsion, an oily gel, an anhydrous gel, a dispersion of vesicles, of microcapsules or of microparticles, or a transdermal device.

The composition according to the invention may also contain the usual adjuvants in cosmetics, such as hydrophilic or lipophilic gelling agents, hydrophilic or lipophilic active agents, thickeners, preserving agents, antioxidants, solvents, fragrances, chelating agents, odor absorbers, chemical or mineral screening agents, mineral pigments, surfactants, polymers, silicone oils and dyestuffs. The amounts of these various adjuvants are those conventionally used in the fields under consideration, and are, for example, from 0.01 to 20% of the total weight of the composition. Depending on their nature, these adjuvants may be introduced into the fatty phase, into the aqueous phase, into the lipid vesicles or into the nanoparticles.

When the composition of the invention is an emulsion, the proportion of the fatty phase may range from 5 to 80% by weight, and preferably from 5 to 50% of the total weight of the composition. The oils, the emulsifiers and the coemulsifiers used in the composition in the form of an emulsion are chosen from those conventionally used in the field under consideration. The emulsifier and the coemulsifier are present, in the composition, in a proportion ranging from 0.3 to 30% by weight, and preferably from 0.5 to 20% of the total weight of the composition.

As oils that can be used in the compositions that make it possible to implement the invention, mention may be made of mineral oils, oils of plant origin (apricot oil, sunflower oil, plum oil), oils of animal origin, synthetic oils, silicone oils and fluoro oils (perfluoropolyethers). Fatty alcohols (cetyl alcohol), fatty acids and waxes (beeswax) can also be used as fatty substances.

As emulsifiers and coemulsifiers that can be used in the invention, mention may, for example, be made of fatty acid esters of polyethylene glycol, such as PEG-40 stearate or PEG-100 stearate, and fatty acid esters of a polyol, such as glyceryl stearate and sorbitan tristearate.

As hydrophilic gelling agents, mention may in particular be made of carboxyvinyl polymers (carbomer), acrylic copolymers such as acrylate/alkyl acrylate copolymers, polyacrylamides, polysaccharides, natural gums and clays, and, as lipophilic gelling agents, mention may be made of modified clays such as bentones, metal salts of fatty acids, hydrophobic silica and polyethylenes.

The methods of administration, the dosages and the optimal pharmaceutical forms of the compounds and compositions according to the invention can be determined according to the criteria generally taken into account in establishing a cosmetic, preferably dermatological, treatment suitable for a patient, for instance the patient's body weight, the excess fat observed, the appearance of the cellulite tissue, the tolerance to the treatment, or the skin type.

The composition according to the invention may contain other active agents, such as soybean peptides, tripeptides consisting of the amino acids glycine, histidine and lysine, mixtures of these peptides and tripeptides, and/or at least one alpha-hydroxy acid of the lactic acid type, in particular for treating and/or preventing stretch marks, or else when the composition is used as an anti-sagging agent for the skin and/or the mucous membranes, or for withstanding the stress under a physical constraint, such as weight gain or a distension of the connective tissues, in particular in the context of a pregnancy.

In a particular embodiment according to the invention, the cosmetic or pharmaceutical composition contains between 0.1 and 10% by weight of a lupeol-rich extract, advantageously between 0.1 and 5% by weight, in particular between 1 and 5% by weight, relative to the total weight of the composition, and also soybean peptides of the hydrolyzed soybean protein type, or tripeptides consisting of the amino acids glycine, histidine and lysine. The soybean peptides or the tripeptides are present in the composition at a content advantageously of between 0.1 and 10% by weight, even more advantageously of between 1 and 5% by weight, even more advantageously of between 2 and 4% by weight, relative to the total weight of the composition. Advantageously, the composition also contains an alpha-hydroxy acid, such as lactic acid. The alpha-hydroxy acid is present in the composition at a content advantageously of between 0.1 and 20% by weight, even more advantageously of between 10 and 15% by weight, relative to the total weight of the composition.

The soybean peptides that are advantageously added to the composition in the context of the present invention may be any peptide obtained by hydrolysis of proteins extracted from soybean, according to operating conditions known to those skilled in the art, in other words, any soybean protein hydrolysate. Preferably, these soybean peptides are peptides that have also been subjected to fermentation with a strain of microorganism. In general, a fermented soybean peptide is obtained by placing a soybean peptide in a fermenter in the presence of glucose, of mineral salts and of a given strain of microorganism, under controlled conditions of temperature, of pH, of oxygenation and of duration. After the fermentation, the fermented soybean peptide is obtained by means of conventional separation and filtration operations. This technique is in particular implemented by the company Coletica, which thus sells various fermented plant protein hydrolysates. Preferably, the fermented or unfermented soybean peptides in the composition used according to the present invention have a molecular weight of between approximately 200 and approximately 20 000 Daltons, as measured, for example, by electrophoresis.

A soybean peptide that is particularly preferred for the composition used according to the invention is the fermented peptide called "Phytokine®", as sold by the company Coletica.

This specific fermented soybean peptide, that has an average molecular weight of approximately 800 Daltons, is obtained by fermentation of a soybean peptide with the Lactobacillus microorganism strain, and its aminogram is as follows:

|  | Number of residues per 100 |
|---|---|
| Hyp | 0.39 |
| Asp | 12.64 |
| Thr | 2.93 |
| Ser | 4.29 |
| Glu | 20.08 |
| Pro | 7.31 |
| Gly | 7.95 |
| Ala | 7.76 |
| Cys | ND* |
| Val | 5.59 |
| Met | 0.96 |
| Ile | 4.46 |
| Leu | 7.42 |
| Tyr | 1.38 |
| Phe | 3.39 |
| His | 2.12 |
| Hyl | 0.09 |
| Lys | 5.73 |
| Trp | ND* |
| Art | 5.53 |
| β-Ala | ND |

(*ND: not determined)

The expression "tripeptides consisting of the amino acids glycine, histidine and lysine" is intended in particular to mean the tripeptides of sequence Gly-His-Lys, the amino acids of which may be in the D, L or DL form, optionally conjugated to a carboxylic acid such as acetic acid, in the form of a complex with a metal such as zinc or copper.

Among the tripeptides consisting of the amino acids glycine, histidine and lysine, use is preferably made of the tripeptide "Kollaren-CPP", the INCI name of which is "tripeptide-1", as sold by the company Seporga. "Kollaren-CPP" is a tripeptide of sequence Gly-His-Lys conjugated to acetic acid (acetate), in the form of a complex with zinc.

The α-hydroxy acid may be any α-hydroxy acid that makes it possible to obtain an exfoliation and/or moisturization effect on the skin, such as, for example, citric acid, pyruvic acid, glycolic acid or else lactic acid.

An α-hydroxy acid that is particularly preferred for the composition used according to the invention is lactic acid.

The composition used according to the invention also advantageously comprises a compound for regulating the pH of the composition according to the invention, at a value of between approximately 2 and approximately 4, and preferably a value of approximately 3.5, in particular for partially neutralizing the α-hydroxy acid. In particular, arginine or an alkanolamine, such as triethanolamine, can be used.

In a particular embodiment of the present invention, the lupeol is obtained from pods of lupin advantageously chosen from the group consisting of *lupinus angustifolius, lupinus albus, lupinus luteus, lupinus mutabilis, lupinus graecus, lupinus micranthus Guss, lupinus hispanicus, lupinus pilosus, lupinus cosentinii, lupinus atlanticus, lupinus princei* and *lupinus somaliensis*. According to an advantageous embodiment of the invention, the lupeol is obtained from pods of *lupinus albus*, preferably *lupinus albus* variety very carrying the pauper gene.

The following examples illustrate the present invention without limiting the scope thereof.

EXAMPLE 1

Composition of a Lupeol-Rich Extract

Table 1 below gives a particular composition of lupeol-rich extract used in the context of the present invention, and also the specifications that a lupeol extract must satisfy in order to be able to be considered as being a lupeol-rich extract according to the present invention.

TABLE 1

| Composition criterion | Results | Specification |
|---|---|---|
| Appearance | Beige to light yellow solid | Beige to light yellow solid |
| Lupeol content (g/100 g) | 84.7 | 75.0–90.0 |
| Total sterols content (g/100 g) | 12.2 | 8.0–20.0 |
| Relative sterols composition (%) | | |
| Beta-sitosterol | 72.9 | 65.0–80.0 |
| Campesterol | 5.7 | 2.0–10.0 |
| Sigmasterol | 21.4 | 15.0–30.0 |
| Loss upon desiccation (g/100 g) (1) | 0.03 | <0.2 |

(1) 1 hour at 105° C.

EXAMPLE 2

Effects of Lupeol on the Expression of the Gene Encoding the HSP47 Heat Shock Protein We used the "cDNA microarray" method for studying the effects of the product on the expression of the genes encoding structural and regulatory proteins of potential interest in skin physiology. Such an approach makes it possible to screen, in a single step, the effects of a product or of a treatment on gene expression in a given biological system and to obtain a signature of the effects of this treatment.

Culture Conditions and Test Products

The product was applied to human skin fibroblasts cultured in MEM/M199 for 18 hours. The lupeol, in solution in ethanol was tested at the concentration of 4.5 µg, this concentration corresponds to a noncytotoxic dose.

Analysis of Differential Gene Expression

The methodology used is that recommended by Clontech (Palo Alto, USA), and comprises:

a step consisting in extracting and purifying the total RNA;

a step consisting in purifying the messenger RNAs according to the AtlasPure protocol (Clontech);

labeling of the DNA probes with $P^{32}$ by reverse transcription;

purifying the label probes by exclusion column chromatography and verification of the quality and of the equivalence by liquid scintillation counting; and hybridizing membranes (provided by the company Custom Atlas BIOAlternative) with the radiolabeled probes (68° C., overnight).

Analysis of Results

The membranes were analyzed by direct quantification of the radioactivity of the spots using a Cyclone PhosphorImager (provided by the company Packard Instrument).

The results are expressed in relative units (RU, mean radioactivity of the points of the double spot corresponding to each gene, corrected for the background noise and for the differences in probe labeling intensity). In this experiment, it was considered, arbitrarily, that a gene was expressed significantly when its RU was greater than or equal to 2.

The results were analyzed case by case, label by label. Arbitrarily, the limit of significance was fixed at approximately +30% of the control for a stimulating effect, i.e. for an effect greater than 130%.

Results

Under our experimental conditions, an incubation for 18 hours in the presence of 4.5 µg/ml of lupeol induces a positive regulation of the expression of the gene encoding HSP47 (cf. table 2).

TABLE 2

| | Control cells | Cells + 4.5 µg/ml lupeol, 18 hours |
|---|---|---|
| RU | 28.2 | 36.4 (129% of the control) |

Conclusion

The results of example 2 suggest that lupeol could, entirely unexpectedly, stimulate the gene encoding the HSP47 heat shock protein in human skin fibroblasts in culture.

EXAMPLE 3

Effects of Lupeol on the Expression of the HSP47 Heat Shock Protein in a Model of Fibroblasts in Culture In order to verify this potential stimulation of HSP47 revealed by the screening, we studied the expression of the HSP47 protein by the Western blotting technique.

This technique consists of:

separation of the various proteins on a polyacrylamide gel under denaturing conditions;

transfer of the proteins onto a specific membrane (PVDF membrane, sold by the company Biorad);

labeling of the protein of interest with a specific antibody (HSP47, Stressgen);

"colorimetric" visualization (Sigma Fast, BCPIP/NBT).

Various nontoxic concentrations (5, 10 and 20 μg/ml) and several incubation times (24 and 48 hours) were tested.

Under our experimental conditions, we recorded a stimulation of HSP47 production for a dose of 20 μg/ml and an incubation time of 48 h.

The inventors have shown, entirely surprisingly, using the microarray technique and the Western blotting technique, that lupeol stimulates HSP47 production at the transcriptional level (mRNA) and at the translational level, i.e. at the protein level.

EXAMPLE 4

Effects of Lupeol on Normal Fibroblasts and Stretch Mark Fibroblasts a) Cells

Normal fibroblasts (FS), fibroblasts from a red or recent stretch mark (FVr) and fibroblasts from an older white stretch mark (FVb) were used in this study.

b) Treatment

The fibroblasts were cultured in the absence or in the presence of lupeol at a concentration of 7 μg/ml.

c) Effect of Lupeol on the Retraction Capacities of Fibroblasts Cultured in a Free Lattice Principle The mechanism of retraction consists of the gathering up and rearranging of collagen by fibroblasts. The collagen polymerizes into fibrils to which the cells attach. The latter pull on the fibrils by virtue of their migratory movement, and thus reorganize the matrix. The diameter of the lattice is then decreased.

Method

The mixture for producing lattices was poured into Petri dishes 50 mm in diameter. A gel formed in a few minutes at 37° C. The lattices were cultured with or without lupeol. The degree of retraction was determined by measuring the diameters of the lattices.

Results

During the first days, the diameter of the gel greatly decreases. The FS retract the matrix more rapidly than the FVr and the FVb. No significant difference is visible between the FVr and the FVb.

The results are given in table 3 below. For example, at D1: the lattices are retracted to 40% of their initial diameter for FS against 29% for FV. The addition of lupeol slows down the retraction. For example, at D2, the lupeol slows down the retraction by 20% for the FS, 20% for the FVr and 10% for the FVb.

TABLE 3

|  | FS | FS + Lupeol | FVr | FVr + lupeol | FVb | FVb + lupeol |
|---|---|---|---|---|---|---|
| Gel diameter | 2.5 | 3 | 3 | 3.6 | 2.9 | 3.2 |
| % decrease in retraction | — | 20 | — | 20 | — | 10 |

Lupeol therefore decreases the retraction capacities of fibroblasts cultured in a collagen lattice.

d) Effect of Lupeol on the Isometric Forces Developed by Fibroblasts Cultured in a Free Lattice Principle Mechanical inhibition of the retraction of the collagen gel in which fibroblasts are embedded is reflected by the generation of a force, called "retraction force" or "isometric force".

The lattices develop in a culture dish that consists of 8 rectangular cells. Placed into each one are 2 flexible silicon slides, the lower parts of which consist of grids to which the lattice attaches when it polymerizes. The lattice develops between 2 slides so as to give a rectangular shape that is slightly shrunken at the center. This shape in conventional mechanics is referred to as a "diabolo" shape. These slides have, in their upper part, a strain gauge system made of gold deposited at their surface. Under the influence of the retraction force developed by the fibroblasts, the silicon slides distort. This is reflected by a variation in the value of electrical resistance of the stress gauge, measured by means of a Wheatstone bridge. This variation indicates the force developed within the lattice, measured in real time via a PC acquisition card and suitable software.

Method

The mixture for producing the lattices was poured into the rectangular cells of the culture dish. A gel formed in a few minutes at 37° C. The DMEMc culture medium with (7 μg/ml) or without lupeol was added. The isometric forces were measured for 48 hours.

Results

Figure 1:
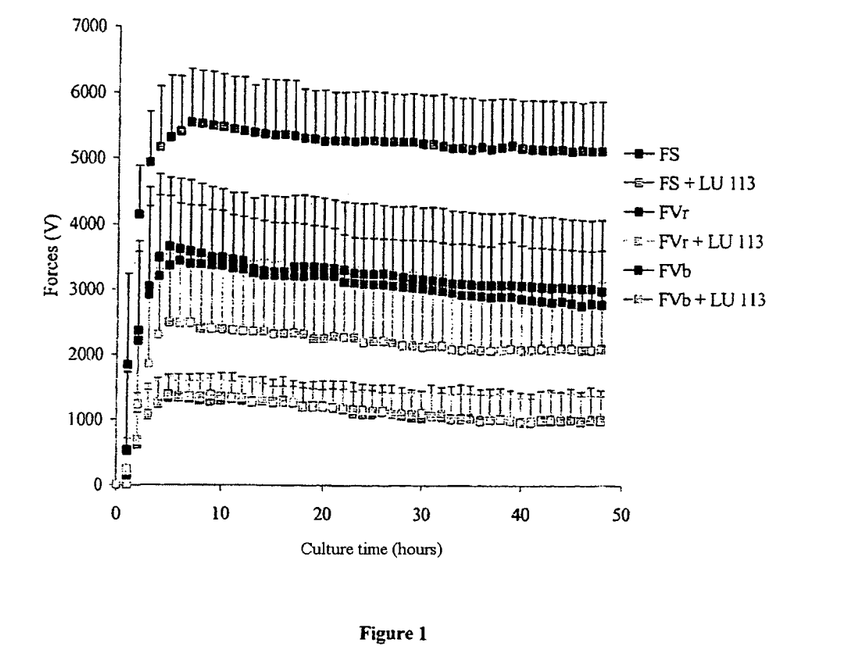
FIG. 1 gives the results of measurement of the isometric forces as a function of culture time.

FIG. 1 gives the results of measurement of the isometric forces as a function of culture time. The isometric forces increase during the first 8 hours of culture. No significant difference is observed between the FS and the FVb. After 7 hours of culture, the FVr develop isometric forces that are significantly greater than those of the FS and FVb (FVr: 5547 V±808; FS: 3583 V±1076; FVb: 3999 V±881). For each of the 3 cell lines, the addition of lupeol significantly decreases the isometric forces (at 7 hours of culture: FVr+LU 113: 2488 V±1065; FS+LU 113: 1325 V±372; FVb+LU 113: 1365 V±228).

Thus, lupeol decreases the isometric forces of normal fibroblasts and fibroblasts from stretch marks (red and white) cultured in a taut lattice.

e) Effect of Lupeol on the Morphology of Fibroblasts Cultured in a Free Lattice

Principle

Fibroblasts are large (100 μm) cells with a fusiform or star-shaped morphology. Their cytoplasm contains an assembly of protein filaments (intermediate filaments, microtubules, actin filaments) which constitute the framework, or cytoskeleton, thereof in close relationship with the plasma membrane. 10% of all cell proteins consist of actin, polymerized in the form of filaments and bundles, which are often described as stress fibers. Actin filaments contribute to the contractile activity of the fibroblast by generating isometric forces. Several types of actin exist, including polymerized fibrillar actin (F actin) and a smooth muscle actin (αSM actin).

Method

1. Demonstration of F Actin

Lattices pulled over a nylon ring were cultured for 5 days in Petri dishes (Ø 50 mm). They were fixed with 3% paraformaldehyde in PBS for 20 min, and then rinsed with PBS. They were subsequently incubated with PBS+0.1% Triton X100 in order to permeabilize the membrane. The lattices were incubated with phalloidin-FITC (2.5 μg/ml) for 30 min in the dark, and rinsed with PBS. They were mounted between slide and cover slip with a drop of Vectashield, and were then observed under a fluorescence microscope, under UV.

2. Demonstration of αSM Actin

Lattices pulled over a nylon ring were cultured for 5 days in Petri dishes (Ø 50 mm). They were fixed with 3% paraformaldehyde in PBS for 20 min, and then rinsed with PBS. They were subsequently incubated with PBS+0.1% Triton X100 so as to permeabilize the membrane with respect to antibodies, and then with 3% H₂O₂ in order to eliminate endogenous peroxidases. A specific binding was blocked with 3% BSA+ 10% sheep serum in PBS. The lattices were subsequently incubated overnight with the mouse anti-αSM actin primary antibody diluted to 1/100, and then rinsed with PBS+BSA. The peroxidase-coupled anti-mouse IgG secondary antibody diluted to 1/150 was applied for one hour and then rinsed with PBS+BSA. The localization of the labeling was revealed with a solution of DAB, which causes the peroxidase to turn black. The lattices were counterstained with Harris hematoxylin for 1-2 min. They were mounted between slide and cover slip and were then observed under an optical microscope.

Results

1. Demonstration of F Actin (cf. FIG. 2)

Figure 2:
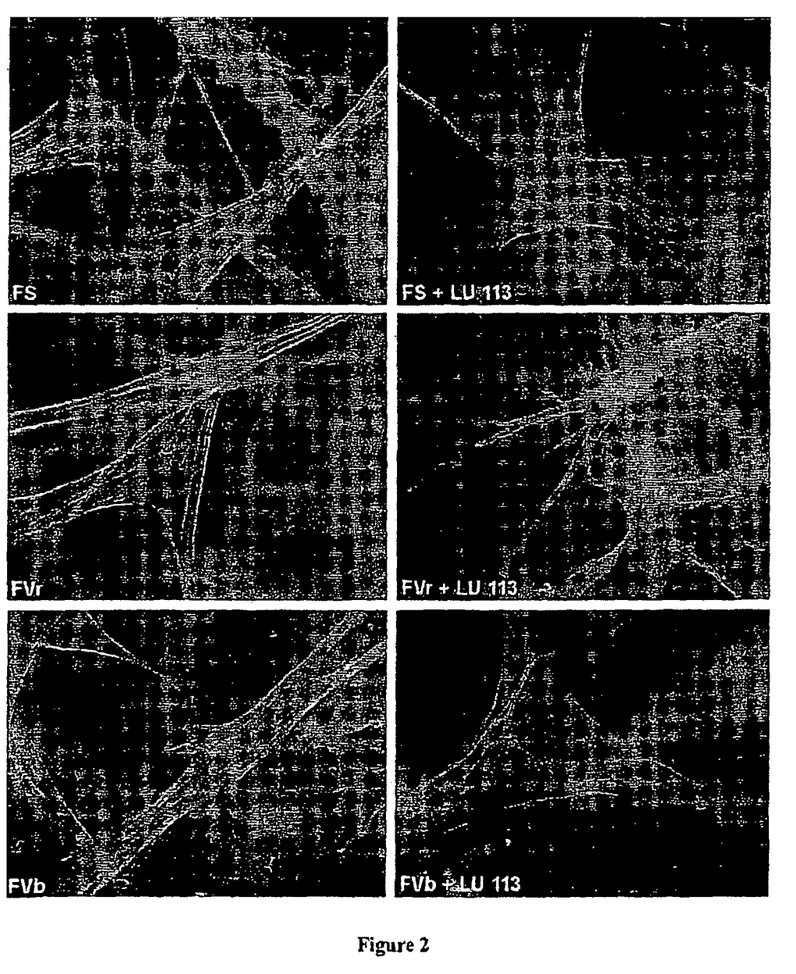
FIG. 2 shows a demonstration of F actin.

The FS, FVr and FVb fibroblasts are elongated and fusiform. Their cytoplasm has F actin stress fibers.

Thus, in the presence of lupeol, the FS, FVr and FVb fibroblasts lose their F actin stress fibers and evolve toward a star-shaped form.

Figure 3:
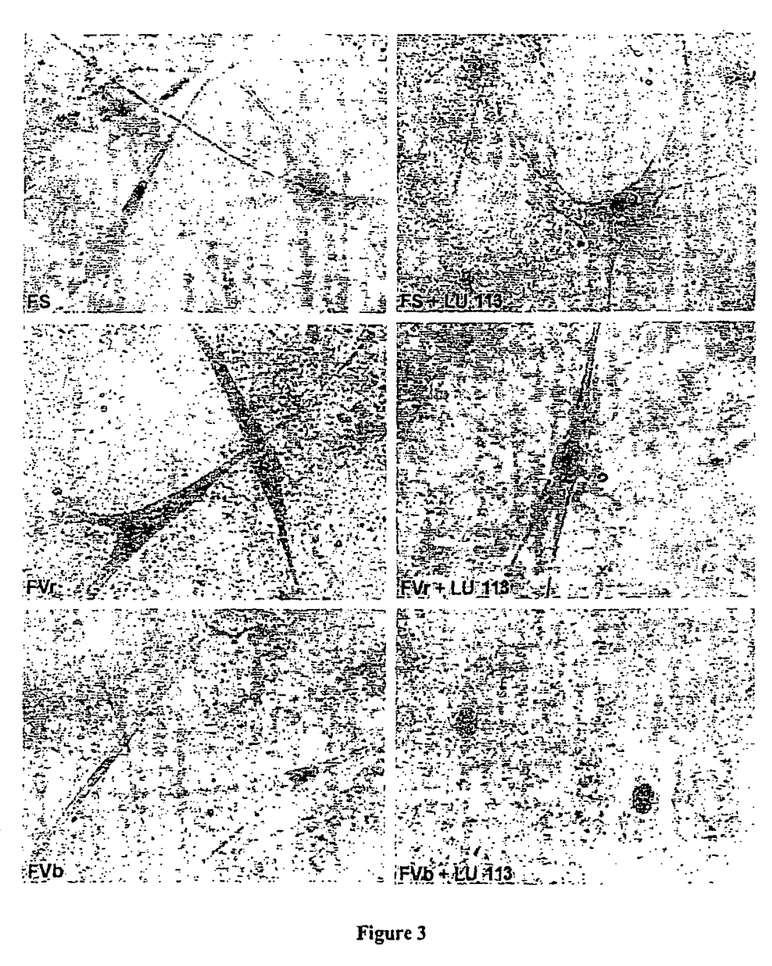
FIG. 3 shows a demonstration of aSM actin.

2. Demonstration of αSM Actin (cf. FIG. 3)

αSM actin, revealed by the brown coloration, is present in granular form in the cytoplasm of the FVr fibroblasts. The FS and FVb fibroblasts contain little αSM actin in granular form.

In the presence of lupeol, the FS, FVr and FVb fibroblasts show weak labeling for αSM actin.

Thus, in the presence of lupeol (active ingredient LU 113), the cytoplasmic distribution of the actin network is not conserved.

f) Conclusion

In conclusion, it has been shown here that lupeol modifies:
the mechanical properties of normal fibroblasts and fibroblasts from stretch marks: retraction capacities and isometric forces,
fibroblast morphology, with an absence of stress fibers.

Stretch marks appear at sites where the skin is subjected to excessive strains and when the dermis becomes fragile, either constitutionally or through metabolic, hormonal or other disorders. The fibroblasts of red stretch marks (recent and evolutive stretch marks) have a considerable contractile capacity, i.e. high isometric forces and a well-developed stress fiber network.

This study shows that lupeol promotes skin decontraction (decrease in isometric forces and in actin fibers), and that its action could therefore be beneficial within stretch marks.

In examples 5 to 10 below, the proportions are given as percentages (w/w), and the abbreviation QS means Quantity Sufficient and the abbreviation QSF means Quantity Sufficient For.

EXAMPLE 5

Mouthwash

| | |
|---|---|
| Lupeol-rich extract | 0.1 to 10% |
| Ethyl alcohol | 10% |
| Glycerol | 10% |
| Ethoxylated hydrogenated castor oil containing 40 mol EO (Cremophor co410) | 0.5% |
| Poly(methyl vinyl ether/maleic acid) (Gantrez S97BF) | 0.2% |
| Sodium hydroxide | 0.15% |
| Sodium fluoride | 0.05% |
| Cinnamon-mint flavoring | 0.1% |
| Triclosan | 0.03% |
| Zinc chloride | 0.01% |
| Sodium saccharin | 0.01% |
| Dye C.I. 16255 (E 124) | 0.0025% |
| Purified water | QSF 100% |

EXAMPLE 6

Toothpaste

| | |
|---|---|
| Lupeol-rich extract | 0.1 to 10% |
| Sodium monofluorophosphate | 0.75% |
| Sodium fluoride | 0.10% |
| 70% sorbitol | 35% |
| Synthetic silica with a high abrasive power | 13% |
| Synthetic silica with a low abrasive power | 5% |
| Sodium carboxymethylcellulose | 1.6% |
| Sodium lauryl sulfate | 1% |
| Mentholated flavoring | 0.85% |
| Titanium oxide | 0.5% |
| Sodium hydroxide lye | 0.5% |
| Sodium cyclamate | 0.3% |
| Menthol | 0.15% |
| Sodium saccharin | 0.07% |
| Purified water | QSF 100% |

EXAMPLE 7

Anti-Stretch Mark Cream

| | |
|---|---|
| Water | QSF 100% |
| Lactic acid | 10.0% |
| Triethanolamine | 7.5% |
| Cyclomethicone | 5.4% |
| Ethylhexyl palmitate | 4.5% |
| Hydrogenated coconut glycerides | 3.0% |
| Sodium lactate methylsilanol | 3.0% |
| Propylene glycol | 2.5% |
| Isodecyl neopentanoate | 2.0% |
| Hydrolyzed soybean protein | 2.0% |
| Glyceryl stearate | 1.7% |
| Arachidyl alcohol | 1.6% |
| Cetyl alcohol | 1.3% |
| Stearic acid | 1.0% |
| Lupeol-rich extract | 0.1 to 10% |
| Behenyl alcohol | 0.9% |
| Polyacrylamide | 0.8% |
| Extract of *Sophora japonica* leaves | 0.5% |
| Arachidic glucoside | 0.4% |
| Beeswax | 0.4% |
| C13–14 isoparaffin | 0.4% |
| DEA cetyl phosphate | 0.3% |
| Zinc gluconate | 0.2% |
| Glycerol | 0.1% |
| Cetearyl alcohol | 0.1% |
| Cetyl palmitate | 0.1% |
| Coconut glycerides | 0.1% |
| Laureth-7 | 0.1% |
| Extract of *Enteromorpha compressa* | 0.1% |
| Fragrance | QS |
| Preserving agents | QS |

EXAMPLE 8

Anti-Stretch Mark Cream

| | |
|---|---|
| Water | QSF 100% |
| Lactic acid | 10.0% |
| Triethanolamine | 7.5% |
| Cyclomethicone | 5.4% |
| Ethylhexyl palmitate | 4.5% |
| Hydrogenated coconut glycerides | 3.0% |
| Sodium lactate methylsilanol | 3.0% |
| Propylene glycol | 2.5% |
| Isodecyl neopentanoate | 2.0% |
| Tripeptides of sequence Gly-His-Lys | 2.0% |
| Glyceryl stearate | 1.7% |
| Arachidyl alcohol | 1.6% |
| Cetyl alcohol | 1.3% |
| Stearic acid | 1.0% |
| Lupeol-rich extract | 0.1 to 10% |
| Behenyl alcohol | 0.9% |
| Polyacrylamide | 0.8% |
| Extract of *Sophora japonica* leaves | 0.5% |
| Arachidic glucoside | 0.4% |
| Beeswax | 0.4% |
| C13–14 isoparaffin | 0.4% |
| DEA cetyl phosphate | 0.3% |
| Zinc gluconate | 0.2% |
| Glycerol | 0.1% |
| Cetearyl alcohol | 0.1% |
| Cetyl palmitate | 0.1% |
| Coconut glycerides | 0.1% |
| Laureth-7 | 0.1% |
| Extract of *Enteromorpha compressa* | 0.1% |
| Fragrance | QS |
| Preserving agents | QS |

EXAMPLE 9

Anti-Stretch Mark Cream

| | |
|---|---|
| Water | QSF 100% |
| Lactic acid | 10.0% |
| Triethanolamine | 7.5% |
| Cyclomethicone | 5.4% |
| Ethylhexyl palmitate | 4.5% |
| Hydrogenated coconut glycerides | 3.0% |
| Sodium lactate methylsilanol | 3.0% |
| Propylene glycol | 2.5% |
| Isodecyl neopentanoate | 2.0% |
| Hydrolyzed soybean protein | 1.0% |
| Tripeptides of sequence Gly-His-Lys | 2.5% |
| Glyceryl stearate | 1.7% |
| Arachidyl alcohol | 1.6% |
| Cetyl alcohol | 1.3% |
| Stearic acid | 1.0% |
| Lupeol-rich extract | 0.1 to 10% |
| Behenyl alcohol | 0.9% |
| Polyacrylamide | 0.8% |
| Extract of *Sophora japonica* leaves | 0.5% |
| Arachidic glucoside | 0.4% |
| Beeswax | 0.4% |
| C13–14 isoparaffin | 0.4% |
| DEA cetyl phosphate | 0.3% |
| Zinc gluconate | 0.2% |
| Glycerol | 0.1% |
| Cetearyl alcohol | 0.1% |
| Cetyl palmitate | 0.1% |
| Coconut glycerides | 0.1% |
| Laureth-7 | 0.1% |
| Extract of *Enteromorpha compressa* | 0.1% |
| Fragrance | QS |
| Preserving agents | QS |

EXAMPLE 10

Restructuring Gel

| | |
|---|---|
| Water | QSF 100% |
| PEG-6 | 3.60% |
| Butylene glycol | 2.70% |
| Dextrin | 1.86% |
| Phenyl trimethicone | 1.20% |
| Lupeol-rich extract | 0.1 to 10% |
| Acrylate/C10–30 alkyl acrylate crosspolymer | 0.60% |
| Dimethicone/phenyl vinyl dimethicone crosspolymer | 0.30% |
| Extract of *Sophora japonica* flowers | 0.20% |
| Xanthan gum | 0.15% |
| PPG 26-Buteth-26 | 0.11% |
| 4,5,7-Trihydroxyisoflavone | 0.10% |
| Hydrolyzed soybean protein | 0.10% |
| Glucose | 0.08% |
| Hydrogenated castor oil PEG 40 | 0.07% |
| Sorbitol | 0.04% |
| Extract of *Centella asiatica* | 0.04% |
| Glycerol | 0.04% |
| Citric acid | 0.02% |
| Extract of *Enteromorpha compressa* | 0.02% |
| Fragrance | QS |
| Preserving agents | QS |

The invention claimed is:

1. A method for improving cicatrisation process, for restructuring the skin and/or the mucous membranes, for treating the sagging of the skin and/or the mucous membranes consisting of administering to a patient in need thereof a composition comprising a lupeol-rich extract obtained from pods of lupin having a lupeol content of between 70 and 100% by weight, wherein said composition comprises between 0.07% and 10% by weight lupeol relative to the total weight of the composition.

2. The method of claim 1, for treating stretch marks or their appearance of a patient.

3. The method of claim 2 wherein said patients are pregnant women.

4. The method of claim 1, wherein said composition is a mouthwash or toothpaste.

5. The method of claim 1, wherein said composition is topically applied.

6. The method of claim 1, wherein the composition comprises between 0.1 and 10% by weight of lupeol-rich extract.

7. The method of claim 1, wherein the lupeol is obtained from pods of *lupinus albus*.

8. The method of claim 7, wherein the lupeol is *lupinus albus* variety Arès carrying the pauper gene.

9. The method of claim 1, wherein the lupeol-rich extract has a total sterol content comprising from 2 to 10% by weight of campesterol, from 15 to 30% by weight of stigmasterol and from 65 to 80% by weight of β-sitosterol.

10. The method of claim 9, wherein the total sterol content is between 8 and 20% by weight of the lupeol rich extract.

* * * * *